United States Patent [19]

Colton

[11] Patent Number: 4,974,728

[45] Date of Patent: Dec. 4, 1990

[54] TRAY HYPODERMIC NEEDLE AND SHARP INSTRUMENTS PROTECTOR

[76] Inventor: Timothy S. Colton, 30 Copper La., Holliston, Mass. 01746

[21] Appl. No.: 432,374

[22] Filed: Nov. 6, 1989

[51] Int. Cl.$^5$ .............................................. B65D 83/10
[52] U.S. Cl. ..................................... 206/366; 206/369
[58] Field of Search ........................ 206/366, 365, 369

[56] References Cited

U.S. PATENT DOCUMENTS

| | | | |
|---|---|---|---|
| 1,625,035 | 4/1927 | Lilly | 206/365 |
| 2,135,279 | 11/1938 | Dickinson et al. | 206/571 |
| 3,207,302 | 9/1965 | Hobbs | 206/366 |
| 3,489,268 | 1/1970 | Meierhoefer | 206/366 |
| 3,727,749 | 4/1973 | Martin | 206/366 |
| 4,383,615 | 5/1983 | Aquino | 206/366 |
| 4,438,845 | 3/1984 | Mochow | 206/366 |
| 4,836,373 | 6/1989 | Goldman | 206/366 |
| 4,844,249 | 7/1989 | Coulombe | 206/365 X |

FOREIGN PATENT DOCUMENTS 2040268  8/1980  United Kingdom ............... 206/366

*Primary Examiner*—William I. Price
*Attorney, Agent, or Firm*—Leon Gilden

[57] ABSTRACT

A hypodermic needle and sharp instruments tray protector is utilized in adhesive or tab-in-slot or snap-in engagement with an upper surface of a surgical tray. The protector defines a sleeve with a forward open end and an aperture directed through a top wall of the sleeve for receiving a cap of a hypodermic needle. The cap is temporarily positioned within the aperture and the needle and sharp instruments directed within the sleeve for preventing inadvertent puncture of an individual during a surgical procedure.

8 Claims, 5 Drawing Sheets

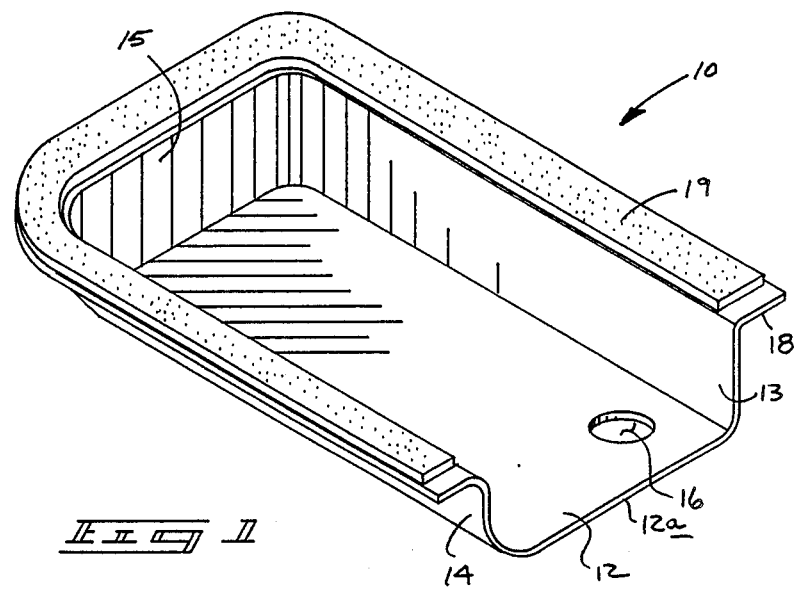
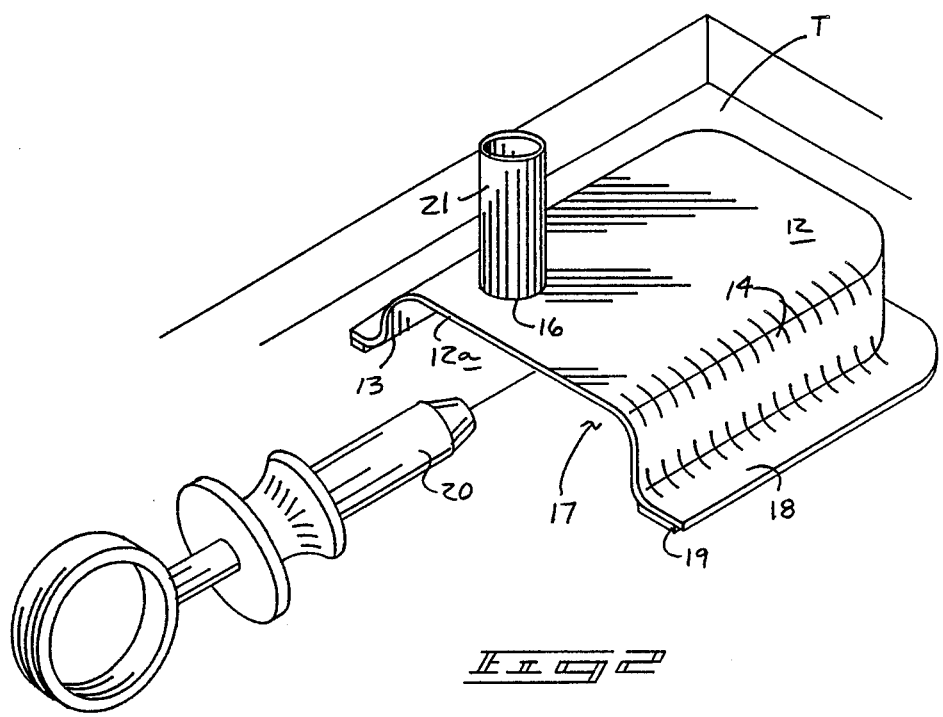

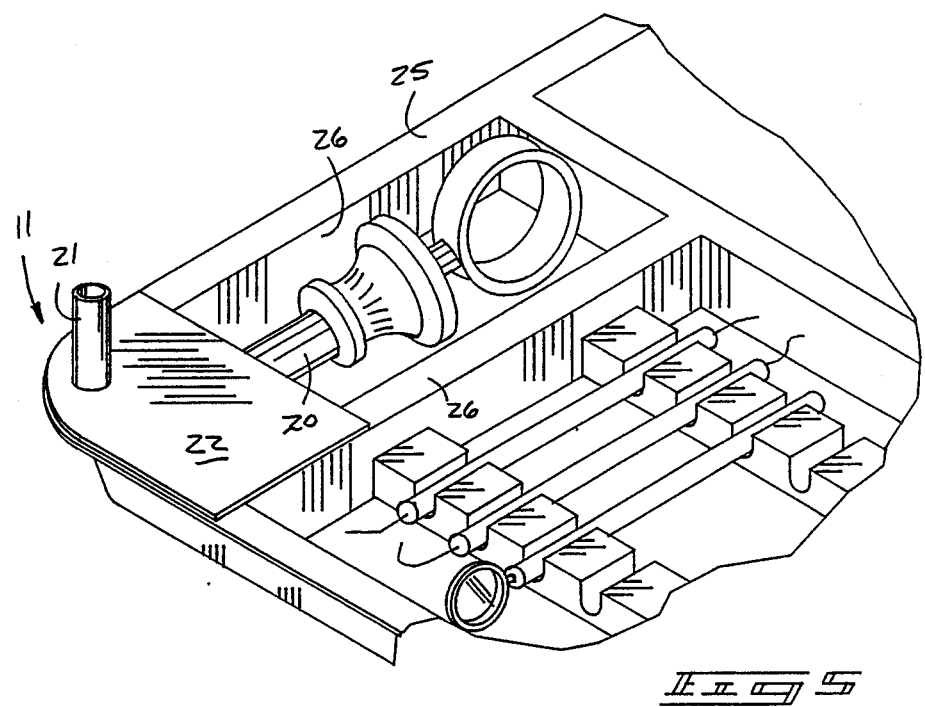
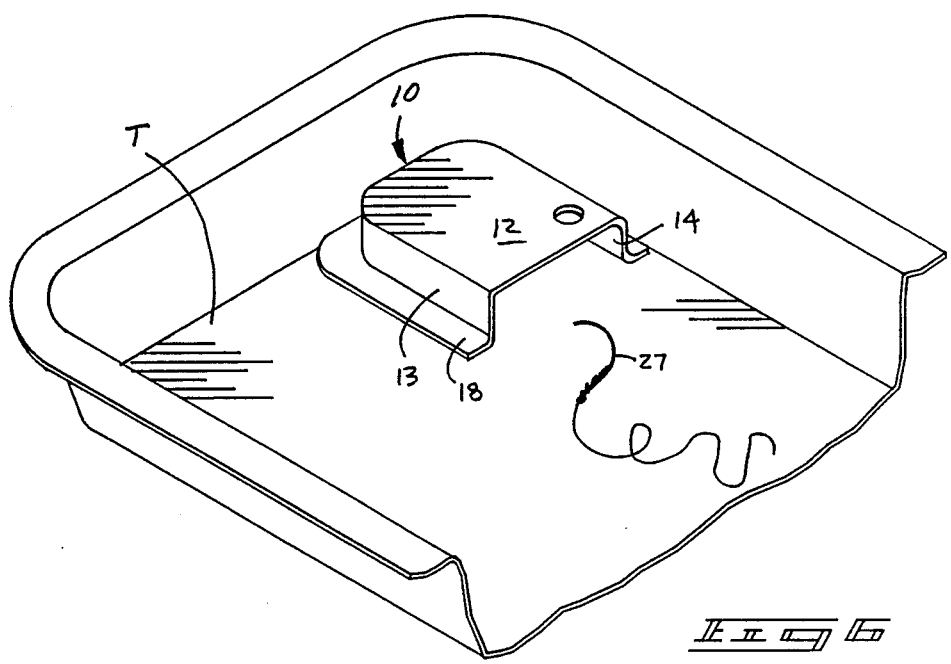

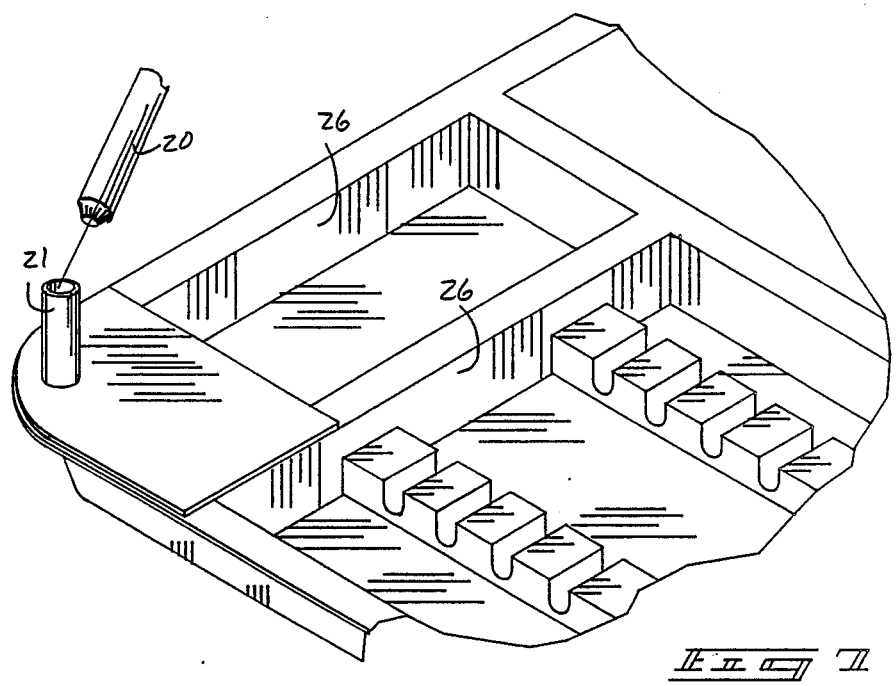
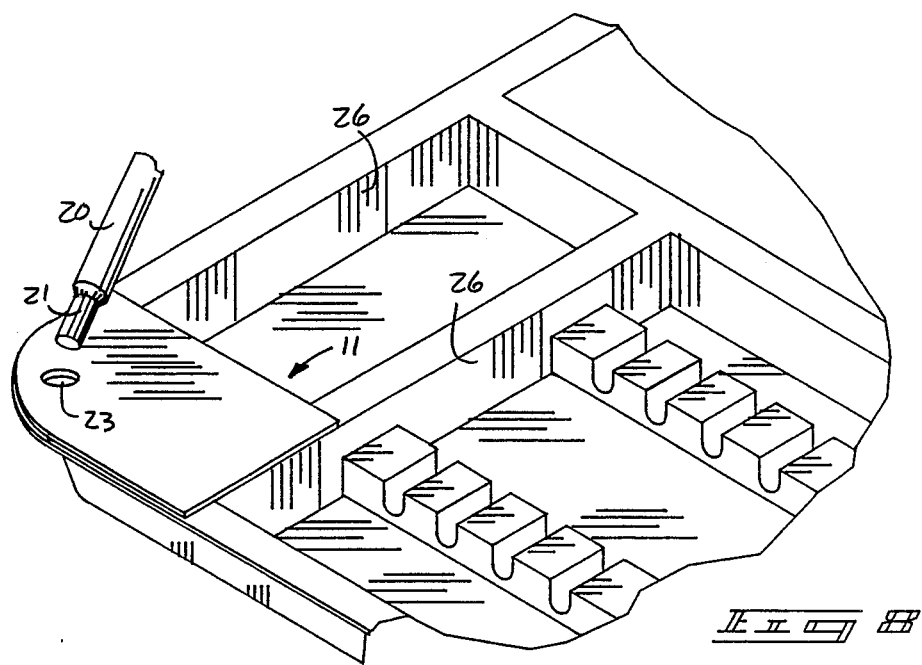

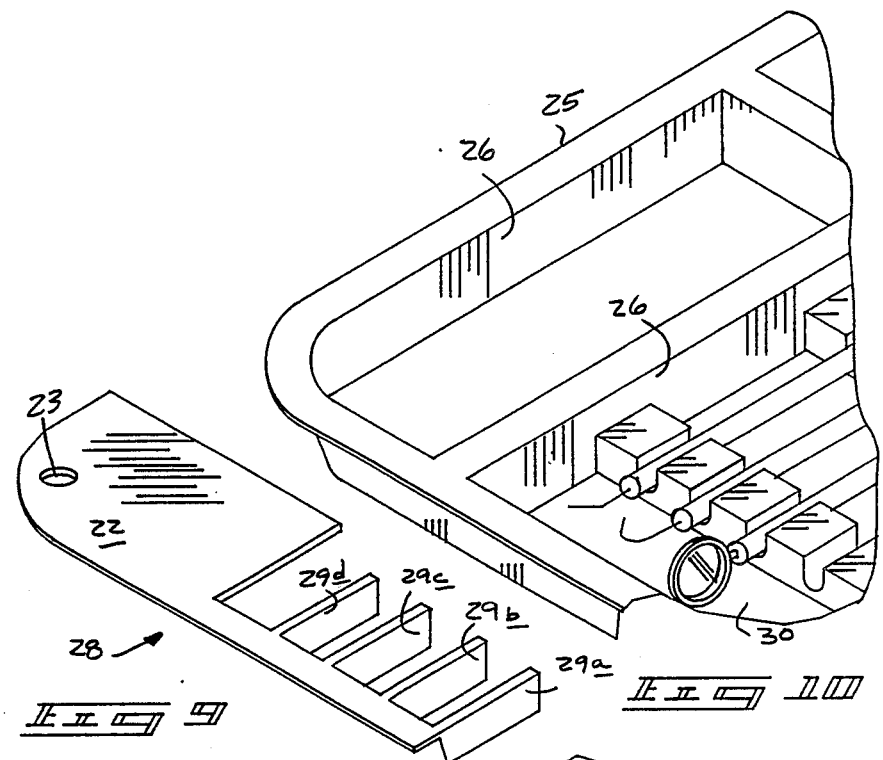
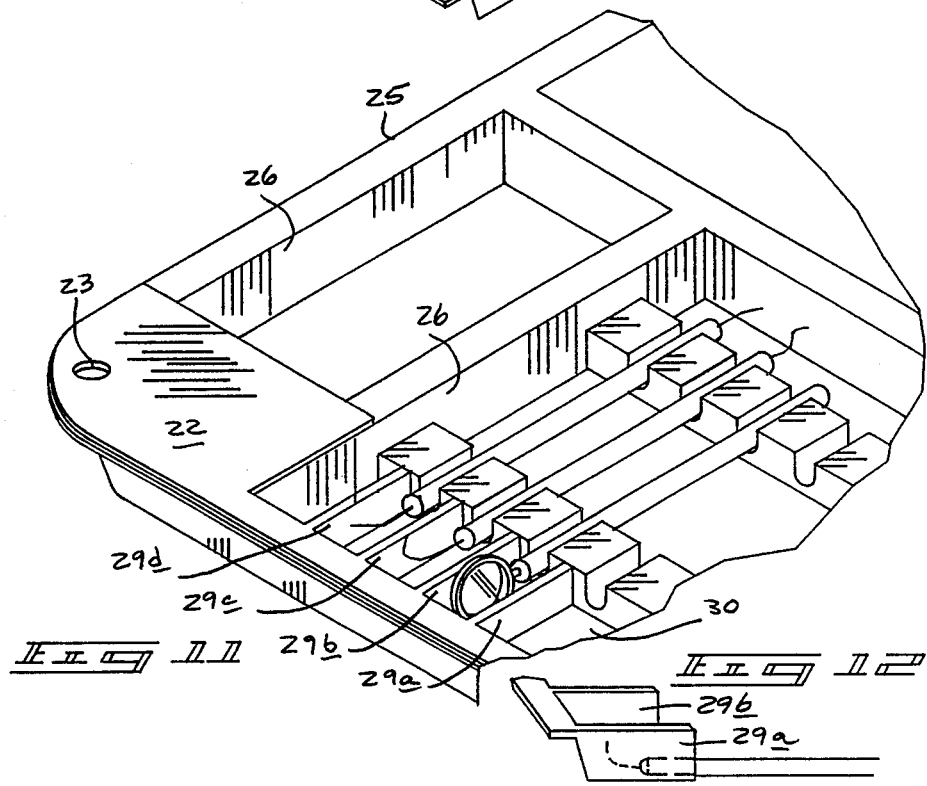

TRAY HYPODERMIC NEEDLE AND SHARP INSTRUMENTS PROTECTOR

BACKGROUND OF THE INVENTION

1. Field of the Invention

The field of invention relates to surgical apparatus, and more particularly pertains to a new and improved hypodermic needle and sharp instruments protector wherein the same is utilized in combination with a surgical tray.

2. Description of the Prior Art

The use of various storage apparatus for hypodermic needles is well known in the prior art. The prior art has heretofore positioned needles within a predetermined geometric array on a surgical tray for use during a medical procedure. The advent of transmitted diseases through cross-contamination by puncture wounds available to surgical personnel and the like has prompted a need for a mechanism to protect individuals from inadvertent contact with a surgical needle and sharp instruments prior to or subsequent to its usage with a medical patient.

Examples of the prior art include U.S. Pat. No. 2,135,279 to Dickinson illustrating a hypodermic needle support tray utilizing a spring-fingered arrangement to secure a forward portion of the hypodermic needle therewithin in a preoriented relationship relative to the tray.

U.S. Pat. No. 3,727,749 to Martin provides for a hypodermic syringe support tray with a series of slotted hoods positioned in a fixedly oriented manner relative to a rear oriented series of cells for securement of hypodermic syringes therewithin.

U.S. Pat. No. 3,489,268 to Meierhoe provides for a packaging of hypodermic needles wherein the package contains a series of cells for orientation of the needles within the package.

U.S. Pat. No. 4,383,615 to Aquino provides for a syringe tray wherein a series of circumferentially spaced sockets frictionally receive the needle portion of a hypodermic syringe to maintain the syringe in a preoriented relationship relative to the tray.

U.S. Pat. No. 4,438,845 to Mochow provides for a package containing hypodermic needles therewithin to maintain the needles in a fixedly secured manner relative to the package.

As such, it may be appreciated that there is a continuing need for a new and improved surgical tray hypodermic needle and sharp instruments protector that is utilized in combination with a surgical tray or incorporated into tray fabrication that addresses both the problems of effectiveness in use, ease of construction, and adaptability to enable orientation of the device in a predetermined manner onto a surface portion of a surgical tray.

SUMMARY OF THE INVENTION

In view of the foregoing disadvantages inherent in the known types of surgical tray apparatus now present in the prior art, the present invention provides a surgical tray hypodermic needle and sharp instruments protector wherein the same utilizes a sleeve construction in combination with a surgical tray for receiving hypodermic needles and sharp instruments therewithin. As such, the general purpose of the present invention, which will be described subsequently in greater detail, is to provide a new and improved surgical tray hypodermic needle and sharp instruments protector which has all the advantages of the prior art surgical tray apparatus and none of the disadvantages.

To attain this, the present invention includes a sleeve-like member including a planar top surface formed with a throughextending aperture at a forward open end thereof defined by downwardly depending side and rear wall portions orthogonally oriented relative to the top wall. A continuous flange is orthogonally directed relative to the side and back wall and extending outwardly therefrom and includes a laminated member adhesively secured thereto with an exposure of a further adhesive surface for securement to an upper surface of a surgical tray. A further surgical tray hypodermic needle and sharp instruments protector includes a generally rectangular portion formed with an arcuate corner for providing a complementary overlying configuration with an arcuate corner of a surgical tray. The member includes a through-extending aperture therethrough with a single continuous adhesive member laminated to three sides of the member, whereupon securement of the member to upper walls of a surgical tray defines a compartment therewithin for receiving the forward end of a hypodermic needle. A further surgical tray "sharps" protector includes contiguously connected multiple vertical planar partitions between the sharp ends of surgical instruments extending above these sharp ends whereupon securement of the member of the tray and the tray's instrument compartment defines multiple open compartments therewithin for receiving the sharp ends of instruments thereby allowing the sharp portions of these instruments to lay in a protectively recessed manner concomitantly allowing visualization as well as easy instrument placement and removal. This invention and its modifications may be made in either reusable or disposable fashion with snap-in, tab-in-slot, or adhesive mechanisms for attachment to surgical trays.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved surgical tray hypodermic needle and sharp instruments protector which has all the advantages of the prior art surgical apparatus and none of the disadvantages.

It is another object of the present invention to provide a new and improved surgical tray hypodermic needle and sharp instruments protector which may be easily and efficiently manufactured and marketed.

It is a further object of the present invention to provide a new and improved surgical tray hypodermic needle and sharp instruments protector which is of a durable and reliable construction.

An even further object of the present invention is to provide a new and improved surgical tray hypodermic needle and sharp instruments protector which is susceptible of a low cost of manufacture with regard to both materials and labor, and which accordingly is then susceptible of low prices of sale to the consuming public, thereby making such surgical tray hypodermic needle and sharp instruments protectors economically available to the buying public.

Still yet another object of the present invention is to provide a new and improved surgical tray hypodermic needle and sharp instruments protector which provides in the apparatuses and methods of the prior art some of the advantages thereof, while simultaneously overcoming some of the disadvantages normally associated therewith.

Still another object of the present invention is to provide a new and improved surgical tray hypodermic needle and sharp instruments protector wherein the same is easily securable to an upper surface of a surgical tray or incorporated directly into tray fabrication for protection of hypodermic needles and sharp instruments and the like utilized in a surgical procedure.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric bottom view of the instant invention.

FIG. 2 is an isometric top view of the instant invention in operative securement to an upper surface of a surgical tray.

FIG. 5 is an isometric illustration of the hypodermic needle and sharp instruments protector, as illustrated in FIG. 4, in operative engagement with an upper surface of a surgical tray.

FIG. 6 is an isometric illustration of the hypodermic needle and sharp instruments protector of FIG. 1 receiving a suturing needle therewithin.

FIG. 7 is an isometric illustration of a hypodermic needle in preparatory engagement with a hypodermic needle cap secured by the instant invention.

FIG. 8 is illustrative of the hypodermic needle and the hypodermic needle cap assembled together and removed from the associated aperture of the hypodermic needle and sharp instruments protector.

FIG. 9 is an isometric illustration of a further "sharps" protector, as utilized by the instant invention.

FIG. 10 is an isometric illustration of a surgical tray with "sharp" instruments about to receive the "sharps" protector.

FIG. 11 is an isometric view of the "sharps" protector, as illustrated in FIG. 9, in operative securement to the upper surface of the surgical tray with instruments.

FIG. 12 is illustrative of a "sharp" instrument laying in a protectively recessed manner within the "sharps" protector.

DESCRIPTION OF THE PREFERRED EMBODIMENT

Figure 3:
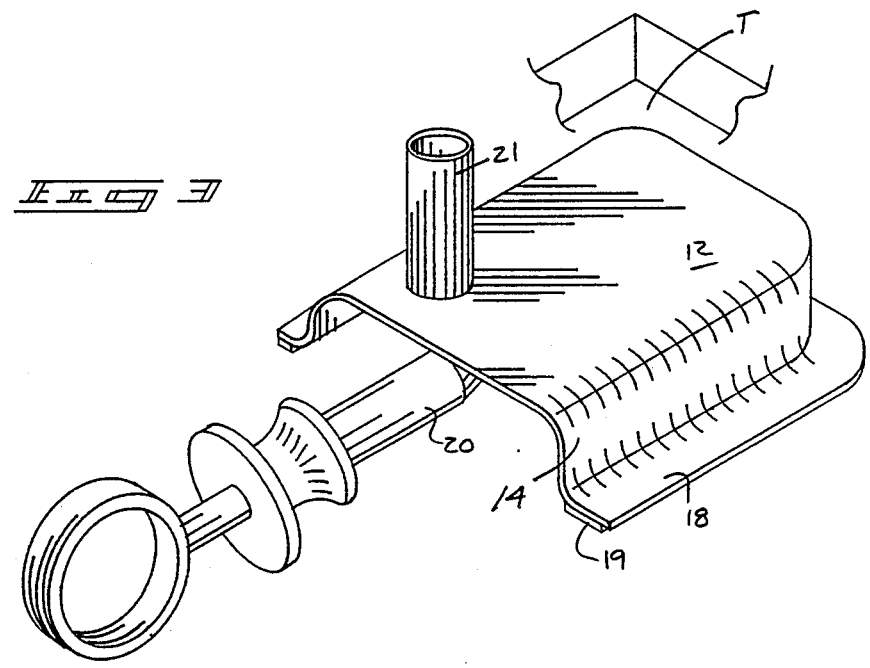
FIG. 3 is a further isometric illustration of the invention, as illustrated in FIG. 2, receiving the forward end of a hypodermic needle therewithin.

With reference now to the drawings, and in particular to FIGS. 1 to 12 thereof, a new and improved surgical tray hypodermic needle and sharp instruments protector embodying the principles and concepts of the present invention and generally designated by the reference numerals 10, 11, and 28 will be described.

More specifically, the surgical tray hypodermic needle and sharp instruments protector 10 essentially comprises a sleeve member defined by a planar top wall 12 with spaced parallel first and second side walls 13 and 14 depending downwardly in an orthogonal manner relative to the top wall with a rear wall 15 defining a continuous side and rear wall surface. A circular aperture 16 is positioned adjacent a forward free edge 12a of the top wall adjacent a forward entrance opening 17. A continuous flange 18 is coextensively formed and orthogonally outwardly directed relative to lower terminal ends of the side and rear walls with an adhesive laminate 19 secured to a bottom surface of the flange 18 exposing an adhesive surface for securement to a surface of a surgical tray "T", as illustrated in FIG. 2 for example. A hypodermic needle 20 and a cylindrical hypodermic needle cap 21 are illustrated in use with the sleeve member, wherein the cap 21 is defined by an external diameter equal to an internal diameter defined by the aperture 16 to receive the cap therewithin. The forward end of the hypodermic needle 20 is directed under the sleeve when the sleeve is secured to the upper surface of the tray, and as illustrated in FIG. 3, completely encompasses the needle portion of the hypodermic needle or syringe to prevent inadvertent puncture wounds that may occur during a surgical or other medical procedure.

Figure 4:
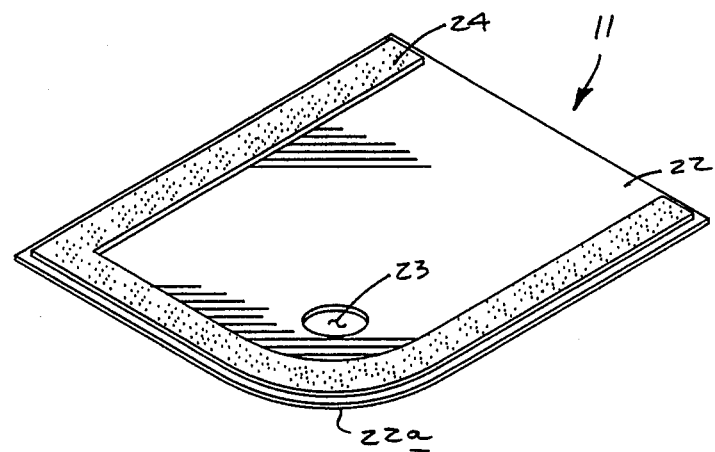
FIG. 4 is a bottom isometric illustration of a further hypodermic needle and sharp instruments protector, as utilized by the instant invention.

FIG. 4 illustrates a further surgical tray hypodermic needle protector 11 defined by a generally planar rectangular panel 22 with a single arcuate corner 22a. The arcuate corner 22a defined by a predetermined radius of curvature equal to that defined by a surgical tray upper flange 25. An aperture 23 is positioned adjacent the arcuate corner and formed orthogonally through the panel 22. In use, the panel 22 and an associated adhesive laminate 24 formed with an exposed adhesive surface is secured to the continuous upper flange of the surgical tray 25 and to spaced upwardly extending tray side walls 26 to define a pocket receiving the hypodermic syringe needle 20 therewithin. The spacing of the tray walls 26 is of a predetermined width equal to the predetermined width of the panel 22. FIG. 6 is illustrative of a suturing needle 27 and its orientation underneath the surgical tray hypodermic needle protector 10 in use.

FIG. 7 illustrates the manner of using the aperture 23 securing the associated hypodermic needle cap therewithin, wherein the hypodermic needle 20 is directed into the cap 21 and thereafter the assembly removed from the aperture 23 without requiring the manual securement of the cap, as is typically necessary, and thereby preventing a further potential for accidental puncture in use of the surgical tools, as illustrated.

FIG. 9 illustrates a further surgical tray sharps protector 28 defined by generally contiguously connected multiple vertical planar partitions 29a through 29d. The partitions 29a through 29d are defined by a predetermined form equal to that defined by the surgical tray instruments receptacle 30. FIG. 10 illustrates a surgical tray with sharp instruments exposed in a hazardous manner. FIG. 11 illustrates the "sharps" protector 28 in operative securement to the upper surface of the surgical tray and the multiple vertical planar partitions 29a through 29d within instrument basin 30. FIG. 12 illustrates the manner of providing protective recess to the surgical sharp instruments by the multiple partitions 29a and 29b.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A surgical tray hypodermic needle and sharp instruments protector device in combination with a surgical tray wherein the tray includes a planar floor and upwardly extending side walls, the device comprising,
 a planar member including an aperture orthogonally directed therethrough defined by a predetermined diameter,
 the planar member including an adhesive means for securement of the planar member to the tray, and
 contiguously connected multiple vertical planar members including securement means for securement of the contiguously connected multiple vertical planar members to the tray.

2. A surgical tray hypodermic needle and sharp instruments protector device as set forth in claim 1 wherein the planar member is defined by a single planar, generally rectangular portion formed with a single arcuate corner with the aperture positioned adjacent the arcuate corner.

3. A surgical tray hypodermic needle and sharp instruments protector device as set forth in claim 2 including a single adhesive strip secured to a bottom surface of the planar member adjacent three side edge portions of the planar member.

4. A surgical tray hypodermic needle and sharp instruments protector device as set forth in claim 3 wherein the arcuate corner is defined by a predetermined radius and the surgical tray is defined by a further arcuate corner defined by further predetermined radius, wherein the further radius is equal to the predetermined radius.

5. A surgical tray hypodermic needle and sharp instruments protector device as set forth in claim 4 wherein the planar member is defined by a predetermined width and wherein the surgical tray includes an outer wall and an inner wall spaced apart a further predetermined width, wherein the predetermined width is equal to the further predetermined width.

6. A surgical tray hypodermic needle and sharp instruments protector device as set forth in claim 5 further including a circular hypodermic needle protector cap receptacle defined by a predetermined diameter, and the aperture defined by a further predetermined diameter and the predetermined diameter equal to the further predetermined diameter of the cap.

7. A surgical tray hypodermic needle and sharp instruments protector device as set forth in claim 1 wherein the contiguously connected multiple vertical planar partitions include spaced planar side walls and planar rear top horizontal connector, and wherein the multiple side walls and the rear top connector define comparments with terminal ends of the side walls and terminal ends of the upper walls defining entrance openings to the compartments.

8. A surgical tray hypodermic needle and sharp instruments protector device as set forth in claim 7 wherein the side walls of the tray terminate at their upper end in a continuous flange, and wherein the securement means includes a single adhesive strip secured to the flange for securement of the protector to the surgical tray with corresponding female slots.

* * * * *